United States Patent [19]
DiBernardo

[11] Patent Number: 5,807,239
[45] Date of Patent: Sep. 15, 1998

[54] TRANSCERVICAL OSTIUM ACCESS DEVICE AND METHOD

[75] Inventor: Dinah DiBernardo, San Jose, Calif.

[73] Assignee: Conceptus, Inc., San Carlos, Calif.

[21] Appl. No.: 649,437

[22] Filed: May 17, 1996

[51] Int. Cl.[6] .................................................. A61B 1/303
[52] U.S. Cl. .............................. 600/135; 600/114; 604/55
[58] Field of Search ...................................... 600/104–105, 600/114, 135, 138, 153, 121; 604/164–165, 158, 264, 55

[56] References Cited

U.S. PATENT DOCUMENTS

| | | | |
|---|---|---|---|
| 3,261,349 | 7/1966 | Wallace | 600/135 |
| 3,669,098 | 6/1972 | Takahashi | 600/114 |
| 3,858,586 | 1/1975 | Lessen | 600/104 X |
| 4,503,843 | 3/1985 | Boebel . | |
| 4,641,634 | 2/1987 | Storz . | |
| 4,688,554 | 8/1987 | Habib | 600/114 |
| 4,696,544 | 9/1987 | Costella | 600/114 X |
| 4,779,612 | 10/1988 | Kishi . | |
| 4,784,117 | 11/1988 | Miyazaki | 600/153 X |
| 4,836,189 | 6/1989 | Alfred, III et al. . | |
| 4,911,148 | 3/1990 | Sosnowski et al. . | |
| 4,924,851 | 5/1990 | Ognier et al. | 600/104 X |
| 4,979,496 | 12/1990 | Komi | 600/114 |
| 5,127,393 | 7/1992 | McFarlin et al. | 600/114 |
| 5,325,845 | 7/1994 | Adair | 600/114 |
| 5,337,733 | 8/1994 | Bauerfiend et al. | 600/114 X |
| 5,372,586 | 12/1994 | Zink et al. . | |

OTHER PUBLICATIONS

Kerin et al., "Development and Application of a Falloposcope for Transvaginal Endoscopy of the Fallopian Tube," *The Journal of Laparoendoscopic Surgery*, 1:47–56 (1990).

Kerin et al., "Falloposcopic Classification and Treatment of Fallopian Tube Lumen Disease," *Fertility and Sterility*, 57(4):731–741 (1992).

Kerin et al., "Falloposcopy: A Microendoscopic Technique for Visual Exploration of the Human Fallopian Tube from the Uterotubal Ostium to the Fimbria Using a Transvaginal Approach," *Fertility and Sterility*, 54(3):390–400 (1990).

Kerin et al., "Tubal Surgery from the Inside Out: Falloposcopy and Balloon Tuboplasty," *Clinical Obstetrics and Gynecology*, 35(2):299–312 (1992).

*Primary Examiner*—Richard J. Apley
*Assistant Examiner*—John P. Leubecker
*Attorney, Agent, or Firm*—Townsend and Townsend and Crew LLP

[57] ABSTRACT

The present invention provides methods, apparatus, and systems for accessing and imaging a patients body lumen, particularly a fallopian tube through an ostium, in a minimally or non-invasive manner. The present invention provides simplified ostium access apparatus and procedures which help to avoid the high cost and large size of known systems having redundant optical scopes for use in the uterine and tubal environments. By separating and independently optimizing the illumination optics from the imaging optics, the present ostium access system is able to make use of the optical image guide of a falloposcope in the substantially larger uterine cavity. As a result, fewer physicians may be required to perform such procedures, in many cases reducing the time, complexity, and, particularly, the cost of such procedures.

9 Claims, 4 Drawing Sheets

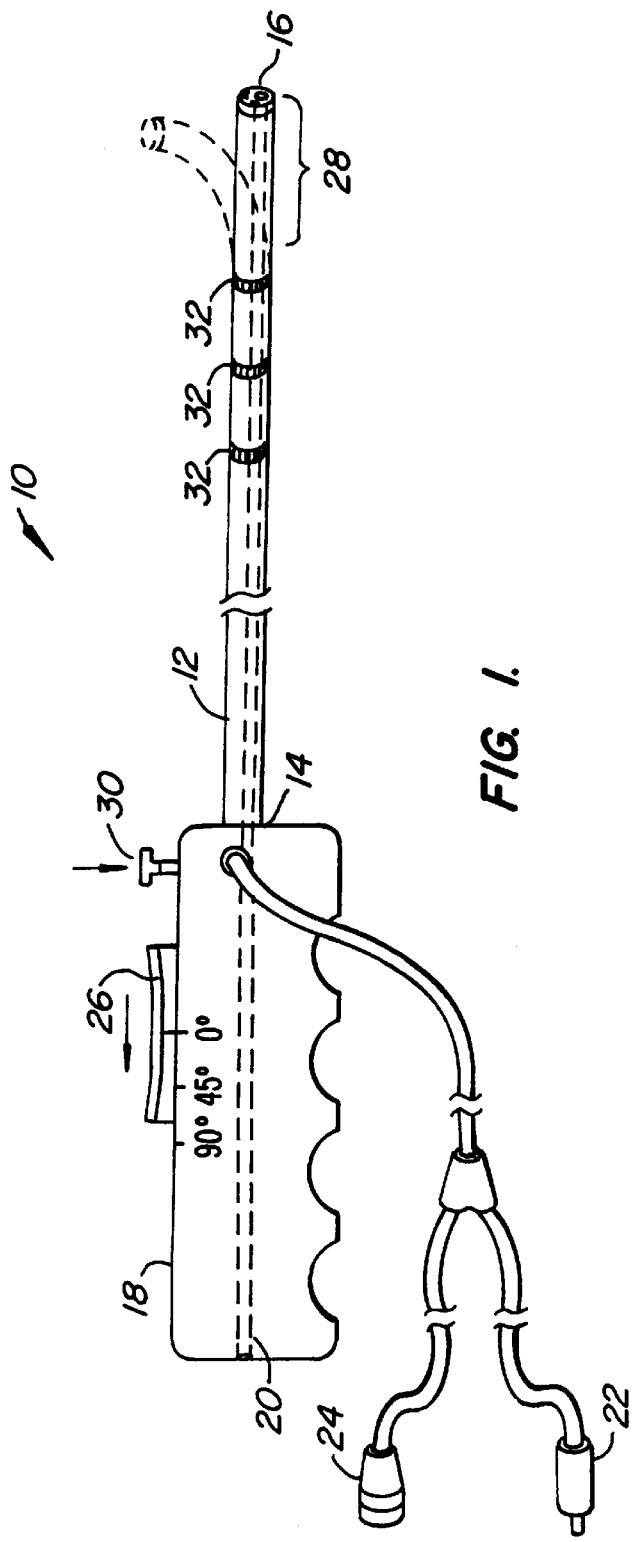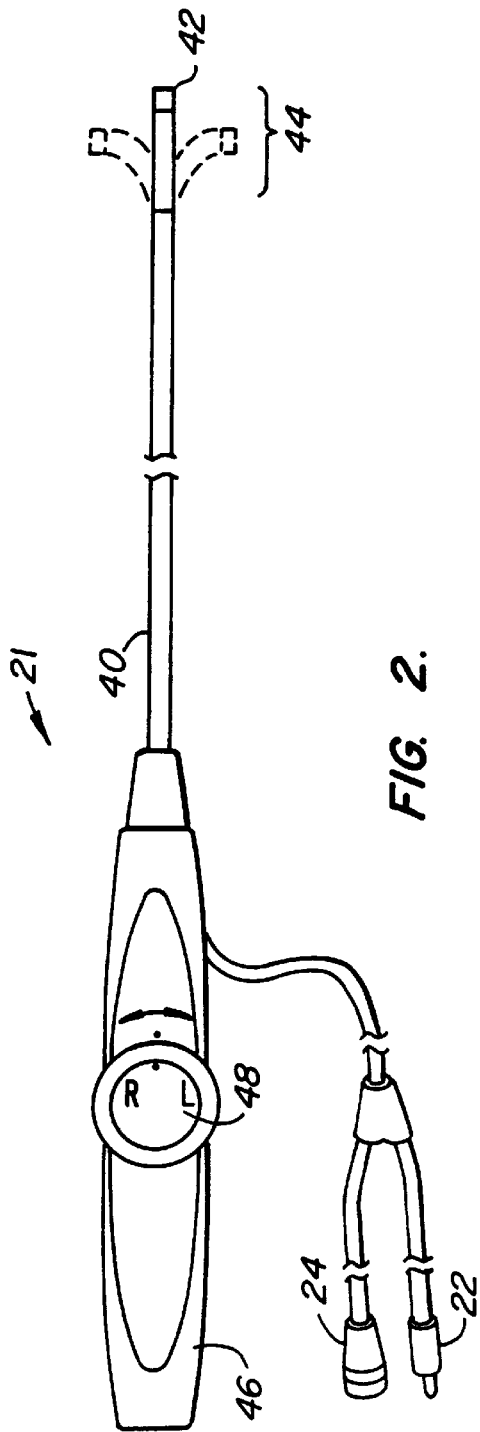

TRANSCERVICAL OSTIUM ACCESS DEVICE AND METHOD

BACKGROUND OF THE INVENTION

Field of the Invention

Present invention relates generally to endoscopic surgical methods and apparatus. More particularly, present invention provides an improved method and system for transcervically accessing the fallopian tubes to facilitate falloposcopic examination and therapies.

Diseases of the fallopian tubes are a major cause of infertility and tubal pregnancy. Until recently, diagnosis and treatment of tubal disease has been hampered by the difficulty in accessing and imaging the interior of the fallopian tubes in a least invasive manner. Such difficulties, however, have been largely overcome by the recent availability of very small guide wires, catheters, and fiber optic viewing scopes, usually refered to as falloposcopes. Using such instruments and systems, a physician can gain atraumatic access to the interior of the fallopian tubes using a hysteroscope positioned within the uterus. Such imaging techniques are described in Kerin, et. al. (1990) *Fertil. Steril.* 54:390–400, and *J. Laparoendoscopic Surg.* 1:47–56.

Such falloposcopic access and imaging techniques are generally performed as follows. A hysteroscope is introduced into the uterus and an irrigation solution introduced to distend the uterus and permit video monitoring. Under the direction of the optical images provided by the hysteroscope, a very small guidewire is then introduced through the hysteroscope and advanced past the ostium into the fallopian tube. The guidewire will continue to be advanced until it approaches the distal fimbria. A small access catheter may then be advanced through the hysteroscope over the guidewire and into the fallopian tube, again preferably reaching the distal fimbria. After removing the guidewire, the falloposcope, a small diameter fiber optic bundle including both imaging and illumination fibers, is advanced until its distal end reaches the distal end of the access catheter. Imaging of the fallopian tube may then be performed in a retrograde manner by drawing the falloposcope and access catheter outwardly through the fallopian tube, and by transmitting the image through the falloposcope for display on an associated video monitor. The access catheter also provides an access lumen for devices, such as direct delivery catheters, small instruments, and the like, for treatment of tubal lumen disease.

While such falloposcopic techniques represent a significant advantage, they still suffer from certain limitations. The techniques require coordination of the hysteroscope, access catheter, and guidewire in order to introduce the access catheter to the fallopian tube, all under the direction of the image provided by the hysteroscope. Once the access catheter is properly positioned and the guidewire is removed and replaced by the falloposcope, attention then shifts to the images provided through the falloposcope. Hence, the optical images of the hysteroscope and falloposcope are used primarily at different stages of the procedure and these systems are, therefore, somewhat redundant.

Unfortunately, the distended uterus and fallopian tubes represent significantly different imaging environments. Clearly, imaging within the fallopian tubes benefits from a thin, highly flexible imaging scope. Furthermore, the falloposcope does not require large amounts of light, as the tubal walls will generally be in quite close proximity to the imaging apparatus. In contrast, imaging within the distended uterine cavity requires substantially greater light to illuminate a larger area of the endometrium from a relatively much greater distance so as to allow the attending physician to locate the ostium within a reasonable time. As the transcervical shaft of the hysteroscope can be made large enough to accommodate both a dedicated hysteroscopic optical imaging system and an independent falloposcope, effective systems and methods for accessing and imaging the fallopian tubes have generally relied upon two separate, independently optimized imaging systems to provide acceptable image quality in each of these regimes.

Nonetheless, there are substantial disadvantages in providing redundant imaging capabilities within a single falloposcopic access system. While the shaft of the hysteroscope can accommodate both image bundles, eliminating one of the image transmission bundles would allow the size of the shaft to be decreased, thereby reducing trauma and increasing maneuverability, possibly even allowing distention of the uterus to be avoided entirely. Furthermore, providing multiple monitors tends to clutter the room in which the procedure takes place, and may also lead to some confusion when attention is shifted back and forth between the monitors. Even more important, as these imaging systems represent a substantial portion of the cost of a fallopian access system, eliminating the redundancy of having two separate optical imaging systems could greatly decrease procedure costs, and increase the availability of these advantageous, minimally invasive falloposcopic procedures.

It would therefore be desirable to provide improved methods and systems for introducing catheters, falloposcopes, and other instruments into the fallopian tubes for diagnosis and treatment. It would be particularly desirable to provide methods and systems for transcervically accessing an ostium and its associated fallopian tube without resorting to multiple independent optical imaging systems. Moreover, it would be desirable to provide a simple, inexpensive, and highly maneuverable ostium access device which could be used with or without distention of the uterus, so as to provide effective access to the fallopian tubes with a minimum of cost and trauma.

DESCRIPTION OF THE BACKGROUND ART

Kerin, et. al. (1990) *Fertil. Steril.* 54:390–400 and *J. Laparoendoscopic. Surg.* 1:47–56, have been described above. Kerin, et. al. (1992) *Fertil. Steril.* 57:731–741 and Kerin and Surrey (1992) *Clin. Obstet. Gynecol.* 35:299–312, describe diagnostic and treatment procedures that can be performed falloposcopically. Hysteroscopes and falloposcopes are described generally in U.S. Pat. Nos. 4,911,148; 4,836,189; 4,799,612; 4,641,634; and 4,503,843. A method and system for performing hysterosalpingography are described in U.S. Pat. No. 5,372,584.

An exemplary method and apparatus for performing hysteroscopic and falloposcopic procedures is described in copending U.S. patent application Ser. No. 08/207,475, filed Mar. 7, 1994, now abandoned in view of copending U.S. patent application Ser. No. 08/703,840, the full disclosure of which is incorporated herein by reference. An exemplary access catheter and method for maintaining separation between a falloposcope and a tubal wall is described in co-pending U.S. patent application Ser. No. 08/544,384, filed Oct. 10, 1995, while U.S. patent application Ser. No. 08/541,987, filed Oct. 10, 1995, describes a protective sheath for a fiber optic image guide within an articulated endoscope. Both of these co-pending U.S. patent applications are also incorporated herein by reference.

SUMMARY OF THE INVENTION

The present invention provides methods, apparatus, and systems for accessing and imaging a patient's body lumen, particularly a fallopian tube through an ostium, in a minimally or non-invasive manner. The present invention provides simplified ostium access apparatus and procedures which help to avoid the high cost and large size of known systems having redundant optical scopes, for use in the uterine and tubal environments. By separating and independently optimizing the illumination optics from the imaging optics, the ostium access system of the present invention is able to make use of the optical image guide of a falloposcope in the substantially larger uterine cavity. As a result of the simplified methods of the present invention, fewer physicians may be required to perform falloposcopic procedures, in many cases reducing the time, complexity, and, particularly, the cost of such procedures. These and other advantages of the present invention will be more apparent from the detailed description of the invention which follows.

In a first aspect, the present invention provides a method for accessing a fallopian tube, the method comprising transcervically introducing an access device into a uterus, and illuminating the uterus with the access device. A falloposcope is introduced through a working lumen of the access device. The access device can then be oriented toward an ostium of the illuminated uterus under the direction of the falloposcope. The falloposcope itself is then advanced from the oriented access device through the ostium and into the fallopian tube. Advantageously, the illuminating optics of the access device remain in the relatively large uterine cavity, while the falloposcope need only include sufficient illumination capability for the much smaller tubal environment. Even more significantly, only a single optical imaging scope is required. In certain embodiments, it may not even be required to distend the uterus during much or all of the ostium access procedure. However, where irrigation or distention is desired, such irrigation may easily be provided through an irrigation lumen of the access device.

In another aspect, the present invention provides an ostium access device for use with a falloposcope having an optical imaging scope and illuminating optical fibers, the access device comprising an elongated tubular shaft having a proximal end, a distal end, and a lumen therebetween. The lumen slidably receives the falloposcope, and an articulating tip disposed at the distal end of the shaft selectively orients the falloposcope toward an ostium of a fallopian tube. A handle at the proximal end of the shaft actuates the articulating tip, and a distal illumination source on the shaft provides illumination within the uterus. Advantageously, the access device need not include an additional, dedicated optical imaging scope, thereby minimizing a cross section of the shaft. Preferably, the articulating tip is selectively deflectable in roughly opposed directions, facilitating accessing of either the two opposed ostia. Optionally, the access device may include an irrigation lumen from adjacent the handle to adjacent the articulating tip. Generally, the illumination source will comprise illuminating optical fibers which articulate with the tip, maximizing the beneficial illumination in the direction it is needed most.

In a still further aspect, the present invention provides a body lumen access system comprising an optical viewing scope and an access device. The scope generally comprises an image guide having a proximal end and a distal end, and illuminating optical fibers having distal ends adjacent the distal end of the image guide. The access device comprises an elongated tubular shaft having a proximal end, a distal end and a lumen therebetween. The lumen slidably receives the scope, and an articulating tip disposed at the distal end of the shaft is capable of selectively orienting the scope toward a lumenal os from within a body cavity. A handle at the proximal end of the shaft actuates the articulating tip, while an illumination source affixed to the shaft provides additional illumination for the scope from the articulating tip. However, the access device does not include an additional optical imaging scope. Hence, such an access system makes efficient use of both the optical imaging system and the available shaft size, as the bulk of illumination fibers (which are beneficial only in the relatively large volume of the body cavity) are not carried unnecessarily with the scope through narrow and tortuous body lumens such as the fallopian tube.

BRIEF DESCRIPTION OF THE DRAWINGS

FIG. 1 is a top view of an ostium access device according to the principles of the present invention.

FIG. 2 is a top view of an alternative ostium access device having a distal tip which can be articulated in either of two roughly opposed directions.

DETAILED DESCRIPTION OF THE SPECIFIC EMBODIMENTS

Figure 3:
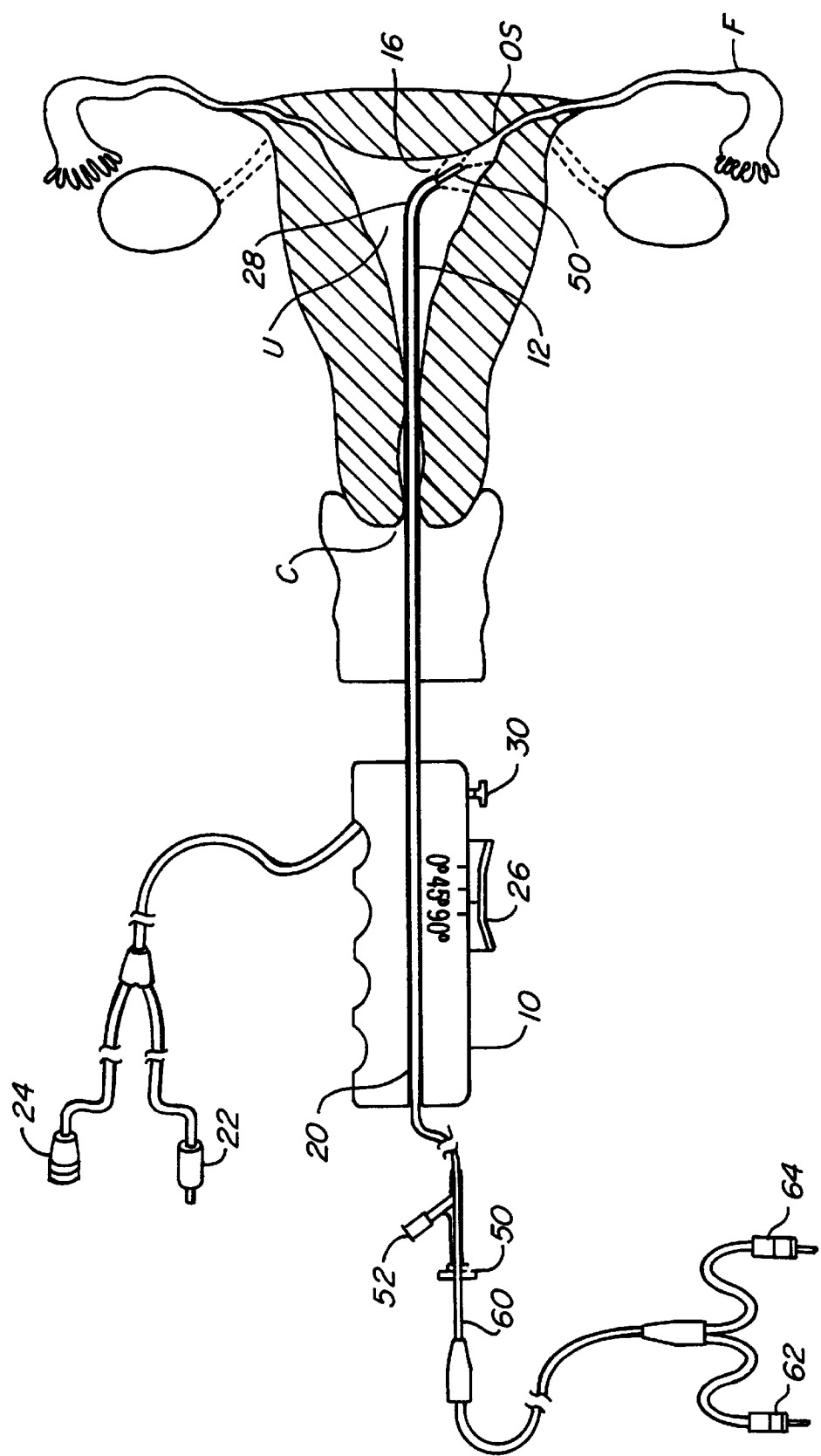
FIG. 3 illustrates a fallopian access system including the ostium access device of FIG. 1, an access catheter, and a falloposcope, wherein the ostium access device is used to illuminate and orient the falloposcope toward the ostium under the optical direction of the falloposcope.

The present invention utilizes an illuminated access device to provide a primary access lumen into a patient's body cavity, typically the uterus. The illuminated access device will provide a primary lumen, and will typically include a proximal handle having a primary lumen port. The handle will also typically allow selective deflection of a distal tip opposite the handle, so as to orient the illumination source and the distal end of the primary lumen towards the target body lumen. However, the access device of the present invention will preferably not include its own dedicated viewing scope, instead relying on the optical imaging capabilities of the falloposcope (or other optical imaging device) which is advanced through the primary lumen.

Referring now to FIG. 1, an ostium access device 10 comprises a working shaft 12 having a proximal end 14 and a distal end 16. A proximal handle 18 is attached to proximal end 14 of shaft 12, and a primary or working lumen 20 extends through the handle 18 and shaft 12 to distal end 16. Shaft 12 further includes illuminating optical fibers and an irrigation lumen, which connect to a conventional illumination source through illumination connector 22, and to a source of irrigation fluid through irrigation connector 24, respectively. The illumination optical fibers and irrigation lumen extend distally through shaft 12 to distal end 16, at which each terminates with a distal orientation.

A pull wire also extends distally from proximal handle 18 through shaft 12 to distal end 16. A slide 26 on proximal handle 18 draws the pull wire proximally so as to manipulate an articulateable tip 28 at the distal portion of shaft 12. Preferably, an articulation scale on the proximal handle indicates the bend angle imposed by the pull wire on the articulateable tip 28, and a locking mechanism 30 is capable of engaging the pull wire to lock the articulateable tip in the desired configuration. While a wide variety of articulation and locking mechanisms may be used, a simple lockeable pull wire is preferred as it provides a reliable and cost effective mechanism for selectively orienting distal tip 16.

Generally, the length of the shaft is between 10 and 30 centimeters, ideally being between about 15 and 20 centimeters. Shaft 12 proximal of articulateable tip 28 may be substantially rigid, but is preferably a semi-rigid or resiliently flexible structure. By eliminating the dedicated optical image transmission mechanism within shaft 12, the outer diameter of the shaft may advantageously be limited to less than 4.4 millimeters. Articulateable tip 28 will generally be between about 2.5 and 3.0 centimeters in length, preferably having a minimum articulation angle of at least 60°, the articulation angle ideally being between about 85° and 90°. To accommodate the falloposcope, the working channel will preferably have an inner diameter of between about 0.04 and 0.07 inches, while the irrigation channel, when it is present, may be between about 0.003 and 0.01 inches in diameter. The light output of the optical fibers from distal tip 16 is preferably at least 0.75 milliwatts, ideally being greater than 1.2 milliwatts, to adequately illuminate the uterine cavity for imaging with the falloposcope. Optionally, a series of shaft markers 32 may be provided to facilitate transcervical positioning of the shaft.

Referring now to FIG. 2, an alternative ostium access device 21 includes features generally similar to the device described above, but here has a shaft 40 including, near a distal end 42, a bi-directional articulateable end 44. Actuation of bi-directional tip 44 is accomplished from proximal handle 46 by using dial 48. A pair of roughly opposed pull wires extend from the dial mechanism to distal end 42 of shaft 44, so that actuation of dial 48 in one direction pulls one pull wire, and so that actuation of dial 48 in the other direction pulls the alternate pull wire. This structure allows bi-directional tip 44 to be selectively deflected towards either ostium from within the uterus. Advantageously, both the amount and the direction of articulation of bi-directional tip 44 will intuitively match the movement of the dial. Furthermore, the locking mechanism may be integrated into the dial, so that pushing down or pulling up on the dial itself locks bi-directional tip 44 in its deflected position.

The ability of alternative ostium access device 20 to articulate in either of two roughly opposed directions provides an increase in functionality, but does require a slight increase in complexity. Hence, the present invention also provides a method for accessing either of the opposed ostia using the ostium access device of FIG. 1. After accessing a first ostium as described below, the device is then rotated about the shaft by roughly 180°. Articulateable tip 28 can then be selectively deflected to access the opposed ostium. Whichever articulation mechanism is used, it is generally preferable to have a locking mechanism which restrains the articulateable tip in its deflected position, the locking mechanism ideally having a simple (push-button) latching and unlatching stroke.

A method for using the ostium access device of FIG. 1 to provide access to the fallopian tubes for imaging or therapy will be explained with reference to FIGS. 3–7. Access through a body cavity to a target body lumen, typically through a uterus to a fallopian tube, will be provided through the working lumen 20 of ostium access device 10 using a small diameter access catheter 50. The structure and use of catheter 50 is more fully explained in co-pending U.S. patent application Ser. No. 08/207,475, previously incorporated herein by reference. Access catheter 50 provides a secondary access lumen in which a falloposcope 60 (or some other fiber optic imaging element) is disposed.

Access catheter 50 typically includes a proximal side port 52 for introducing irrigation fluid through the lumen of the catheter body. By passing a clear irrigation fluid through side port 52 and distally around the falloposcope 60, the fallopian tube F may be distended and imaging quality of the falloposcope may be enhanced. As more fully explained in co-pending U.S. patent application Ser. No. 08/544,384, filed Oct. 10, 1995, the full disclosure of which is incorporated herein by reference, distal end 56 of catheter 50 may also include one or more elements which extend axially beyond distal end 66 of falloposcope 60 to maintain separation between the tubal walls and the imaging optics. Such an axially extending structure may also be advantageous for use with the fallopian access system of the present invention, as it facilitates advancement of the falloposcope and access catheter together without having a pre-positioned guidewire, the axially extending structure acting somewhat as a distal guidewire tip.

Figure 7:
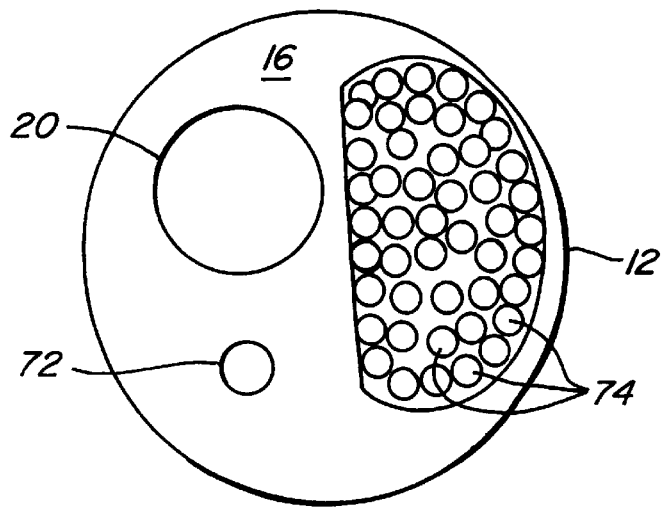
FIG. 7 is a detailed view of the distal end of the ostium access device of FIG. 1.

When using the access system of the present invention, shaft 12 of ostium access device 10 is positioned transcervically by inserting distal end 16 through the cervical os C. Optionally, insertion of ostium access device 10 may be directed with reference to positioning markers 32. Falloposcope 60 is then inserted into access catheter 50, and the access catheter 50 is in turn passed through working lumen 20 of ostium access device 10. Optionally, the uterus may be distended by introducing irrigation fluid through irrigation connector 24, the irrigation fluid passing through an irrigation lumen along the shaft and exiting shaft 12 at irrigation port 72, as seen in FIG. 7. Distention of the uterus is facilitated by providing some cervical sealing mechanism on shaft 12. In some embodiments of the present inventive method, distention of the uterus may not be required.

Once ostium access device 10 and falloposcope 60 are positioned with their distal ends extending into the uterus U, the uterus may be illuminated through illumination connector 22. Typically, light will also be provided by the illumination optical fibers of the scope itself, as supplied through scope illumination connector 62. Typically, however, imaging will be provided solely by the falloposcope 60 as transmitted to conventional image monitoring equipment through image connector 64. By making use of the illumination capabilities of both the scope and access device, the scope may be used to image the relatively large volume of the uterine cavity. Manipulation of the ostium access device 10, and particularly, varying the angle of actuateable tip 28, is then used to locate the ostium OS.

Figure 6:
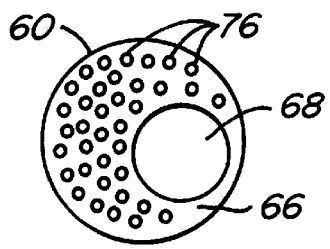
FIG. 6 is a detailed view of the distal end of the falloposcope.

The internal illumination provided by the access device 10 and the falloposcope 60 can be understood with reference to FIGS. 3, 6, and 7. An optical imaging lens 68 and a plurality of optical illumination fiber bundles 76 can be seen at the distal end 66 of falloposcope 60, as illustrated in FIG. 6. A coherent image fiber optic bundle transmits the image from optical imaging lens 68, down the falloposcope, and eventually to the viewing monitor or eye piece. The image itself actually comprises the illumination light from illumination fibers 76 which is reflected by objects located within a field of view of the distal end of the falloposcope. If either insufficient or excessive light is reflected to the imaging lens, the imaging apparatus is unable to produce a coherent picture. It is generally preferable to include the least possible number of illumination optical fibers required for imaging, as including excessive fibers will make falloposcope 60 large in diameter, stiff, and thereby, unable to easily traverse the narrow and often tortuous fallopian tube. Fortunately, a relatively small amount of illumination is required in the near field tubal environment to provide effective falloposcopic imaging.

To allow falloposcope 60 to also provide imaging within the more far field uterine environment, illuminating optical fibers 74 are provided at distal end 16 of shaft 12, as can be seen in FIG. 7. These optical fibers provide a light source which will be oriented in the same direction as working lumen 20. Hence, illumination fibers 74 of optical access device 10 and illumination fibers 76 of falloposcope 60 may be used together to provide sufficient illumination to properly orient the working lumen 20 toward the ostium OS. Once the working lumen is properly oriented, set screw 30 locks articulateable tip 28 in the proper configuration. Access catheter 50 and falloposcope 60 may then be advanced distally from the position ostium access device, through the ostium OS, and along the fallopian tube F. Optionally, ostium access device 10 may be immobilized during advancement of the falloposcope. Where distention is not required, this may be accomplished simply by attaching ostium access device 10 to a speculum.

Figure 4:
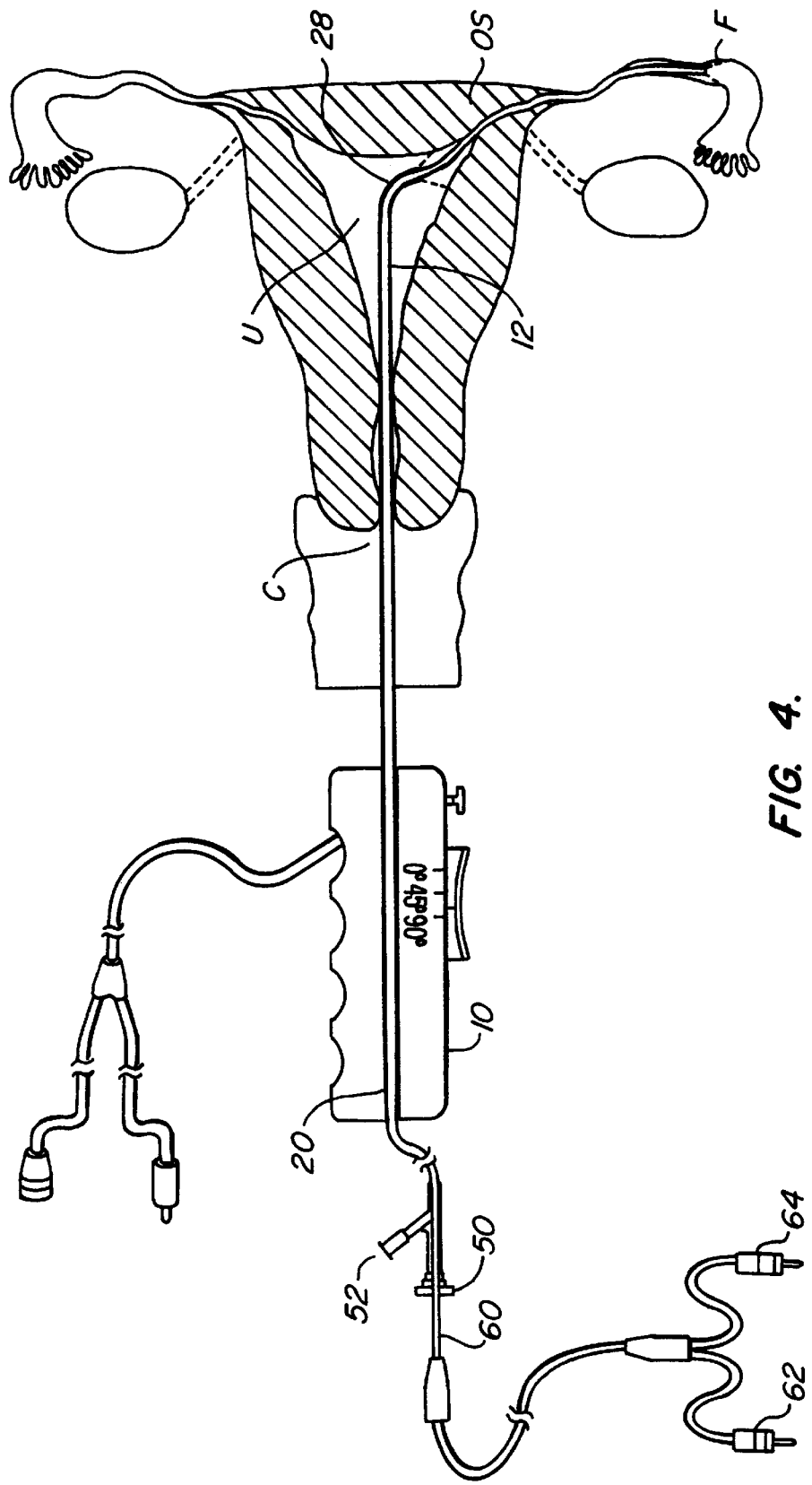
FIG. 4 illustrates the fallopian tube access system of FIG. 3 after the access catheter and falloposcope have been advanced into the fallopian tube so that all illumination is provided by the falloposcope.
Figure 5:
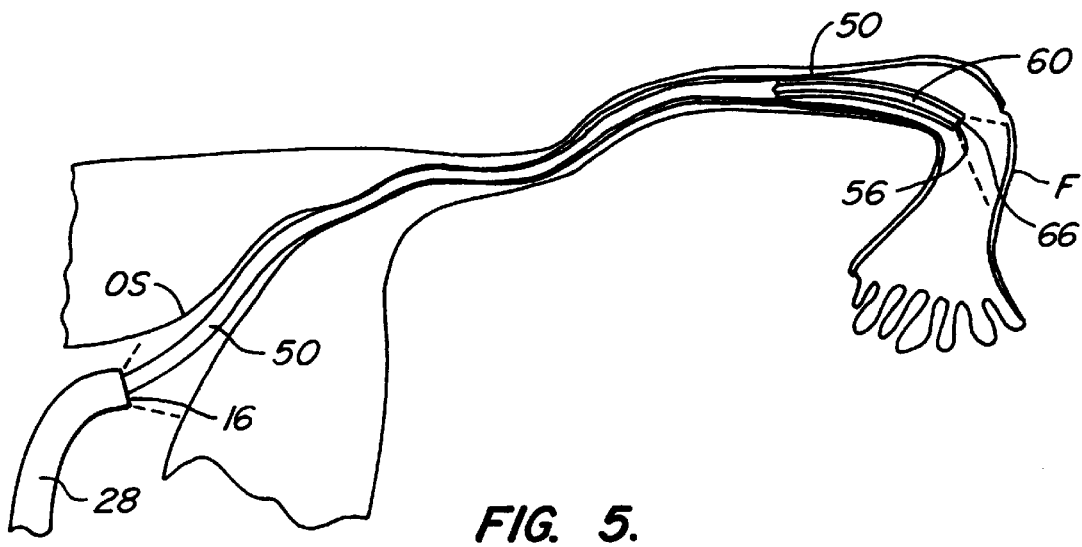
FIG. 5 is a detailed view of the access catheter and falloposcope within the fallopian tube, and also shows the distal end of the ostium access device within the uterus.

The independent use of falloposcope 60 within the fallopian tube can be seen most clearly in FIGS. 4, 5, and 6. The access catheter and scope have here been advanced beyond the illumination provided by the ostium access device 10. However, as less light is needed for imaging, good image quality can be maintained by the illumination fiber optics 76 of falloposcope 60. The viewing scope will generally be extendable at least 10 cm beyond the access device.

It may also be possible to utilize optical imaging to direct the advancement of the access catheter 50 and falloposcope 60 along fallopian tube F. Where the access catheter and falloposcope are advanced together, the method and system of the present invention avoids the separate steps of first advancing a guidewire, advancing an access catheter over the guidewire, removing the guidewire from within the access catheter, and then advancing the falloposcope through the access catheter, as required for known falloposcopic retrograde imaging methods. Alternatively, it may be possible to access the ostium using the ostium access device of the present invention, but to then replace the falloposcope with a guidewire at any time to traverse a narrow or difficult portion of the fallopian tube. Such a method still avoids the cost and complexity of having two scope systems, and therefore provides a substantial improvement over known falloposcopic techniques.

Although the foregoing invention has been described in some detail by way of illustration and example, for purposes of clarity and understanding, it will be obvious that certain changes and modifications may be practiced within the scope of the appended claims.

What is claimed is:

1. A method for accessing a fallopian tube, the method comprising:

transcervically introducing an access device into a uterus;

illuminating the uterus with the access device;

introducing a falloposcope through a working lumen of the access device, the access device lacking an optical imaging device which is separate from the falloposcope;

orienting the access device toward an ostium of the illuminated uterus under the direction of the falloposcope;

advancing the falloposcope distally beyond the oriented access device through the ostium and into the fallopian tube; and imaging the fallopian tube with the falloposcope while illuminating the fallopian tube with the falloposcope.

2. A method as in claim 1, wherein the orienting step comprises optically imaging the uterus with only the falloposcope.

3. A method as in claim 1, wherein the falloposcope is oriented toward the ostium at least in part by selectively deflecting a tip of the access device in a first direction.

4. A method as in claim 3, further comprising orienting the access device toward an alternative ostium of the illuminated uterus under the direction of the falloposcope by selectively deflecting the tip of the access device in a second direction roughly opposite the first direction.

5. A method as in claim 3, further comprising releasably restraining the deflected tip of the oriented access device.

6. A method as in claim 1, wherein the uterus is not distended during the orienting step.

7. A method as in claim 1, further comprising irrigating the uterus through an irrigation lumen of the access device.

8. A method as in claim 1, wherein the illuminating step comprises illuminating the uterus with the falloposcope while illuminating the uterus with the access device.

9. A method as in claim 8, wherein more light is provided for illuminating the uterus than for illuminating the fallopian tube.

* * * * *